United States Patent
Jung et al.

(10) Patent No.: US 12,053,303 B2
(45) Date of Patent: Aug. 6, 2024

(54) MANUFACTURING METHOD FOR A MULTIELECTRODE SYSTEM

(71) Applicant: Heraeus Deutschland Gmbh & Co. KG, Hanau (DE)

(72) Inventors: Markus Jung, Hanau (DE); Oliver Keitel, Aschaffenburg (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 1004 days.

(21) Appl. No.: 16/358,123

(22) Filed: Mar. 19, 2019

(65) Prior Publication Data

US 2019/0290206 A1 Sep. 26, 2019

(30) Foreign Application Priority Data

Mar. 23, 2018 (EP) .................................. 18163684

(51) Int. Cl.
*A61B 5/01* (2006.01)
*A61B 5/00* (2006.01)
(Continued)

(52) U.S. Cl.
CPC ............ *A61B 5/6851* (2013.01); *A61B 5/287* (2021.01); *A61B 5/6858* (2013.01);
(Continued)

(58) Field of Classification Search
CPC ..... A61B 5/6851; A61B 5/287; A61B 5/6858; A61B 5/6859; A61B 18/1492;
(Continued)

(56) References Cited

U.S. PATENT DOCUMENTS

| 6,071,281 A | 6/2000 | Burnside et al. |
| 8,005,544 B2 * | 8/2011 | Zhu ...................... A61N 1/3627 607/9 |

(Continued)

FOREIGN PATENT DOCUMENTS

EP 0964720 12/1999

OTHER PUBLICATIONS

Non-Final Office Action is U.S. Appl. No. 16/358,115 dated Jul. 29, 2020.

(Continued)

*Primary Examiner* — Rex R Holmes
(74) *Attorney, Agent, or Firm* — Dicke, Billig & Czaja, PLLC (57) ABSTRACT

One aspect includes a manufacturing method for a multielectrode system including providing several conductors, which are electrically conductive in their longitudinal direction; bundling the conductors at a proximal portion of the multielectrode system by means of a sheath surrounding the conductors to form a conductor bundle configured to be used as a lead of the multielectrode system; and providing several ring electrodes each surrounding one of the conductors at a distal portion of the multielectrode system and electrically connecting the ring electrodes and the conductors to form a multielectrode array of the multielectrode system. The multielectrode array is configured to be in a longitudinally extended or in a transversally expanded configuration.

16 Claims, 5 Drawing Sheets

(51) Int. Cl.
    *A61B 5/287*     (2021.01)
    *A61B 18/14*     (2006.01)
    *A61N 1/05*     (2006.01)
    *A61N 1/36*     (2006.01)
    *A61N 1/372*     (2006.01)
    *A61N 1/375*     (2006.01)
    *A61B 18/00*     (2006.01)

(52) U.S. Cl.
    CPC ........ *A61B 5/6859* (2013.01); *A61B 18/1492* (2013.01); *A61N 1/05* (2013.01); *A61N 1/0551* (2013.01); *A61N 1/0587* (2013.01); *A61N 1/36125* (2013.01); *A61N 1/37205* (2013.01); *A61N 1/37512* (2017.08); *A61B 2018/0016* (2013.01); *A61B 2018/00267* (2013.01); *A61B 2018/00357* (2013.01); *A61B 2018/00577* (2013.01); *A61B 2562/125* (2013.01)

(58) Field of Classification Search
    CPC .. A61B 2018/0016; A61B 2018/00267; A61B 2018/00357; A61B 2018/00577; A61B 2562/125; A61N 1/05; A61N 1/0551; A61N 1/0587; A61N 1/36125; A61N 1/37205; A61N 1/37512
    See application file for complete search history.

(56) References Cited

U.S. PATENT DOCUMENTS

| | | |
|---|---|---|
| 8,533,944 B2 | 9/2013 | Swanson |
| 9,079,018 B2 | 7/2015 | Olsen |
| 2003/0093072 A1 | 5/2003 | Friedman |
| 2011/0106074 A1 | 5/2011 | Kunis et al. |
| 2011/0137382 A1 | 6/2011 | Swanson |
| 2011/0166569 A1 | 7/2011 | Whayne et al. |
| 2013/0338745 A1 | 12/2013 | Ollivier et al. |
| 2014/0107455 A1 | 4/2014 | Régnier et al. |
| 2014/0296951 A1 | 10/2014 | Vetter et al. |
| 2016/0073960 A1 | 3/2016 | Jung et al. |
| 2016/0235967 A1 | 8/2016 | Shan et al. |
| 2018/0161577 A1* | 6/2018 | Goedeke .............. A61B 5/7246 |
| 2019/0021620 A1 | 1/2019 | Olson et al. |

OTHER PUBLICATIONS

Final Office Action is U.S. Appl. No. 16/358, 115 dated Dec. 17, 2020.

Notice of Allowance for U.S. Appl. No. 16/358,115 dated Mar. 10, 2021.

\* cited by examiner

MANUFACTURING METHOD FOR A MULTIELECTRODE SYSTEM

CROSS-REFERENCE TO RELATED APPLICATION

This Utility Patent Application claims priority to Application No. EP 18 163 684.6, filed on Mar. 23, 2018, which is incorporated herein by reference.

TECHNICAL FIELD

One embodiment relates to a manufacturing method for a multielectrode system, the multielectrode system, a multielectrode unit including such multielectrode system and a use of such multielectrode system or multielectrode unit.

BACKGROUND

US2013338745 A1 relates to a multipolar lead for implantation in a venous, arterial, or lymphatic network, and for use with an electric stimulation or detection device. The multipolar lead includes at least two microcables, each having a central conductor for connection to the electric stimulation or detection device. The multipolar lead further includes a first ring having at least two lumens, each sized to receive a microcable of the at least two microcables, wherein one of the at least two lumens is a connection lumen which receives a first microcable of the at least two microcables. The ring further includes a connection element movable into the connection lumen to pierce a sheath of the first microcable and to press into the central conductor of the first microcable received by the connection lumen, electrically connecting at least a portion of the first ring to the central conductor.

The structure and manufacture of such device is rather complicated. There may be a need to provide an improved manufacturing method for a multielectrode system, which is easier and/or more flexible.

SUMMARY

It should be noted that the aspects of one embodiment described in the following apply also to the manufacturing method for a multielectrode system, the multielectrode system, the multielectrode unit including such multielectrode system and the use of such multielectrode system or multielectrode unit.

According to one embodiment, a manufacturing method for a multielectrode system is presented. The manufacturing method includes the following:
a) providing several conductors, which are electrically conductive in their longitudinal direction,
b) bundling the conductors at a proximal portion of the multielectrode system by means of a sheath surrounding the conductors at least partially to form a conductor bundle configured to be used as a lead of the multielectrode system, and
c) providing several ring electrodes each surrounding one of the conductors at least partially at a distal portion of the multielectrode system and electrically connecting the ring electrodes and the conductors to form a multielectrode array of the multielectrode system,
wherein the multielectrode array is configured to be in a longitudinally extended configuration or in a transversally expanded configuration.

This can be understood in that the multielectrode system includes a longitudinally extending lead and a multielectrode array. The lead can be understood as a cable or coil. The multielectrode array can be understood as an area including several (independent) electrodes that can stimulate, detect and/or the like.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

The multielectrode array can change between a longitudinally extended configuration, for example, an insertion process into a lumen, and a transversally expanded configuration, for example, an operation modus. The transversally expanded configuration can be understood as a spherically or ball-shaped, conically or cone-shaped or otherwise expanded configuration. It can be understood as a partially open configuration including accessible slits between adjacent conductors. Further below, some options to have the multielectrode array switch between a longitudinally extended and a transversally expanded configuration are illustrated.

The present manufacturing method for a multielectrode system is less complex than conventional manufacturing methods and allows manufacturing multielectrode systems, which are more reliable and long-term stable than multielectrode systems manufactured according to conventional manufacturing methods system. For example, an improved corrosion resistance may be achieved in comparison to a multielectrode system manufactured by a conventional thin-film process.

Further, the present manufacturing method is flexible and may provide multielectrode systems with various shapes and sizes of ring electrodes and exposed ring electrode portions.

Additionally, an improved multielectrode array can be manufactured, because the transversally and for example, spherically or conically expanded configuration has a partially open shape including free slits between adjacent conductors. These slits are accessible for tissue, nerve cells, drugs, molecules etc. and prevent that the multielectrode system acts as a harmful barrier that prevents ingrowth, diffusion etc. and increases the risk of inflammatory reactions that are dangerous and detrimental for stimulation or detection by the multielectrode array.

Further, an improved multielectrode system can be manufactured, which is very small with respect to its diameter to avoid injuries of a venous, arterial, or lymphatic network, in which it is to be inserted. A diameter of a multielectrode system manufactured according to the present manufacturing method can be below or equal to 1.2 mm and in one embodiment below or equal to 1 mm. In an example, a diameter of the multielectrode system is in a range between 0.25 and 2.5 mm and in one embodiment in the range between 0.5 and 0.85 mm.

The present manufacturing method allows manufacturing such small multielectrode systems with still a high number of electrodes. A number of exposed ring electrode portions can be in the range of 2 to 300 and in one embodiment 2 to 36. In an example, a diameter of the multielectrode system is in a range between 0.5 and 2.5 mm and the multielectrode system includes between 2 and 150 ring electrodes. In one embodiment, a diameter of the multielectrode system is between 0.5 and 1.2 mm and the multielectrode system includes between 2 to 36 ring electrodes.

The ring electrodes arranged at the conductor may be configured to be individually addressed. For example, the ring electrodes arranged along one conductor including a strand of several wires or a bundle of several strands including several wires may be electrically isolated in a direction perpendicular to its longitudinal direction and may therefore be electrically connected to the conductor independently from each other. In other words, the ring electrodes may be electrically isolated in a direction perpendicular to the longitudinal direction of the conductor to be electrically independent to each other. This arrangement can for example, apply to a transversally expandable portion of the multielectrode array. As a result, the different ring electrodes may be electrically isolated relative to each other and can therefore be electrically contacted and controlled independently of each other. Consequently, the different ring electrodes may be individually addressed.

The electrodes may still have large electrode surfaces, which allow using less current densities, which again avoid injuries of the venous, arterial, or lymphatic network.

As a result, the present manufacturing method for a multielectrode system allows manufacturing a multielectrode system, which is smaller in diameter and effective cross-section than a conventional multielectrode system not only during insertion but also during operation. The effective cross-section is reduced by the open configuration, which reduces the barrier function within the body.

The term "conductor" can be understood as a (single) wire, a strand of several wires or a bundle of several strands including several wires. The conductor is electrically conductive in a direction along its longitudinal direction. The conductor may be an insulated conductor, which is electrically insulated in a direction perpendicular to its longitudinal direction. The electrical insulation may be a coating around the conductor and/or a wire, strand or bundle within the conductor.

In an example, the bundling is a heating of the sheath. The sheath can be a heat shrink.

A ring electrode surrounding the conductor can be understood in that the ring electrode at least partially or completely surrounds the conductor or covers a circumference ring of the conductor at least partially or completely. The ring electrodes can have various shapes and are in one embodiment round or angular with or without rounded corners.

In an example, the electrical connecting of the ring electrode with the conductor is a welding, gluing, mechanically pressing, crimping or the like.

There are several options to have the multielectrode array configured to be in a longitudinally extended configuration or in a transversally and for example, spherically/conically/otherwise expanded configuration. The transversally, spherically, conically or otherwise expanded configuration may be a rest position of the multielectrode array.

In an example, the transversally expanded configuration is changeable into the longitudinally extended configuration by inserting the multielectrode array in a sleeve or a catheter and for example, by pushing the multielectrode array in the sleeve or catheter or pulling the multielectrode array through a sleeve or a catheter. The transversally expanded configuration can then be changeable into the longitudinally extended configuration by removing the sleeve or catheter from the multielectrode array.

Additionally or alternatively, the manufacturing method for a multielectrode system further includes:
  providing a tube extending within the conductor bundle,
  providing a guidewire extending within the tube and the multielectrode array, and
  attaching the guidewire to a distal tip portion of the multielectrode system so that a pulling of the guidewire leads to a change of the multielectrode array from the longitudinally extended to the transversally and for example, spherically expanded configuration.

This can be understood in that the tube does not extend into the multielectrode array, so that only the guidewire extends into the multielectrode array. The lead may be inserted into a body lumen by means of the guidewire and a catheter. After positioning, the guidewire may be retracted, so that the multielectrode array opens and changes from the longitudinally extended to the open and transversally expanded configuration. The guidewire can be electrically insulated by for example, using a suitable bulk material or a coating.

Additionally or alternatively, the conductors include, are coated with or are made of a shape memory alloy configured to have a longitudinally extended and a transversally and for example, spherically/conically/otherwise expanded configuration.

Additionally or alternatively, the conductors are coated with a polymer, which is able to be thermally shaped to be configured to have a longitudinally extended and a transversally and for example, spherically/conically/otherwise expanded configuration. The thermally shaped polymer (for example, PU, ETFE, Polyimide, etc.) can be thermally shaped during manufacturing. Thermal shaping can be understood in that a polymer coated multielectrode array is formed to a sphere or cone or any other transversally expanded configuration by inserting a spherical or conical or otherwise transversally expanded template in between the lines, heating the compound and removing the template. The spherical or conical or otherwise transversally expanded shape remains. During insertion into a lumen by means of for example, a catheter, the multielectrode array is straightened. By removing the catheter, the multielectrode array expands and the spherical, conical or otherwise transversally expanded structure opens.

In an example, the manufacturing method for a multielectrode system further includes:
  providing the sheath around the conductors also in the distal portion of the multielectrode system, and
  partially removing the sheath to expose at least a ring electrode portion of one of the ring electrodes.

In an example, the partial removing of the sheath from the ring electrode(s) is a laser ablation, a mechanical cutting or the like. The exposed ring electrode portions can be configured, for example, stimulation, detection and/or the like. In an example, an outer diameter of a ring electrode is in a range between 20 and 1000 μm and in one embodiment between 100 and 400 μm. A wall thickness of such ring electrode can be in the range of 10 to 200 μm and in one embodiment 20 to 50 μm. A number of exposed ring electrode portions, sub-electrodes or windows can be in the range of 1 to 300 and in one embodiment 1 to 36. The exposed ring electrode portions may have a surface between 0.01 and 5 mm$^2$ and in one embodiment between 0.01 and 2 mm$^2$.

The exposed ring electrode portions can have various shapes and are in one embodiment round. The ring electrode portions can be at least partially arranged axially above each other, but also all other arrangements are possible. The high number of ring electrode portions and the various possible shapes allow a very efficient therapy.

In an example, the manufacturing method for a multielectrode system further includes:
  providing at least one conductor and one ring electrode in the distal portion of the multielectrode system at least partially with a sub-sheath, and
  partially removing the sub-sheath to expose at least a ring electrode portion of the ring electrode.

In an example, the manufacturing method for a multielectrode system further includes:
  electrically connecting either at least one of the conductors and/or the guidewire with a distal tip portion of the multielectrode system to form a tip electrode of the multielectrode system.

The distal tip portion of the multielectrode system can however also be only mechanically connected to the conductors and the guidewire, so that the distal tip portion does not form an additional electrode.

According to one embodiment, also a multielectrode system is presented. The multielectrode system includes:
  several conductors, which are electrically conductive in their longitudinal direction,
  a sheath surrounding the conductors at least partially to form a conductor bundle configured as a lead of the multielectrode system, and
  several ring electrodes each surrounding one of the conductors at least partially at a distal portion of the multielectrode system, wherein the ring electrodes are electrically connected to the conductors to form a multielectrode array of the multielectrode system,
  wherein the multielectrode array is configured to be in a longitudinally extended or in a transversally expanded configuration.

The transversally, spherically, conically or otherwise expanded configuration has a partially open shape including free slits between adjacent conductors, which are accessible for tissue, nerve cells, drugs, molecules etc. and prevent that the multielectrode system acts as a harmful barrier that prevents ingrowth, diffusion etc. and increases the risk of inflammatory reactions that are dangerous and also detrimental for stimulation or detection by the multielectrode array.

The present multielectrode system is not too complex in manufacture and therefore not too expensive. Further, it is more reliable and long-term stable with an improved corrosion resistance than multielectrode systems manufactured according to conventional (thin film) manufacturing methods.

Various shapes and sizes of the multielectrode system and its ring electrodes and exposed ring electrode portions can be easily provided. The multielectrode system can be provided with a very small diameter to avoid injuries of a venous, arterial, or lymphatic network. A diameter of a multielectrode system manufactured according to the present manufacturing method can be below or equal to 1.2 mm and in one embodiment below or equal to 1 mm. A diameter of the lead may be below or equal to 1 mm and in one embodiment in the range between 0.25 and 0.85 mm. Such small multielectrode systems can still be provided with a high number of electrodes. A number of exposed ring electrode portions can be in the range of 2 to 300 and in one embodiment 2 to 36.

In an example, the ring electrodes arranged at one of the conductors may be individually addressed. In other words, the ring electrodes arranged along one conductor including a strand of several wires or a bundle of several strands may be electrically connected to the conductor independently from each other.

In an example, a diameter of the multielectrode system is in a range between 0.5 and 2.5 mm and the multielectrode system includes between 2 and 150 ring electrodes. In one embodiment, a diameter of the multielectrode system is between 0.5 and 1.2 mm and the multielectrode system includes between 2 to 36 ring electrodes.

The electrodes may still have large electrode surfaces, which allow using less current densities, which again avoid injuries of the venous, arterial, or lymphatic network.

As a result, the present multielectrode system might be smaller in diameter than a conventional multielectrode system during insertion as well as also during operation when it comes to a barrier function within the body.

In an example, at least one of the several conductors is an insulated conductor, which is electrically insulated in a direction perpendicular to its longitudinal direction. The electrical insulation may be a coating around the conductor and in one embodiment a polymer coating. A thickness of the electrical insulation of a conductor may be between 3 and 150 μm and in one embodiment between 12 and 40 μm.

In an example, at least one of the several conductors is a wire.

In an example, at least one of the several conductors is a strand of several wires.

In an example, at least one of the several conductors is a bundle of several strands including several wires.

In an example, at least one of the wires or one of the strands is electrically insulated in a direction perpendicular to its longitudinal direction.

In an example, the strand and/or the bundle is at a proximal portion of the multielectrode system bundled and at least partially surrounded by means of a strand and/or bundle sheath surrounding the strand and/or bundle.

In an example, the strand and/or the bundle includes a sub-guidewire, which may further ease the pulling back of the (sub-) guidewire(s) and the change of the multielectrode array from the longitudinally extended to the transversally and for example, spherically expanded configuration.

There are several options to have the multielectrode array configured to be in a longitudinally extended or in a transversally, spherically or conically expanded configuration. The transversally, spherically or conically expanded configuration may be a rest position of the multielectrode array.

The transversally, spherically or conically expanded configuration may be changeable into the longitudinally extended configuration by inserting the multielectrode array into a sleeve or a catheter.

Additionally or otherwise, the multielectrode system may further include a tube extending within the conductor bundle and a guidewire extending within the tube and the multielectrode array. The guidewire can be attached to a distal tip portion of the multielectrode system so that a pulling of the guidewire leads to a change of the multielectrode array from the longitudinally extended to the transversally and for example, spherically expanded configuration. The lead may be inserted into a body lumen by means of the guidewire and a catheter. After positioning, the guidewire may be retracted, so that the multielectrode array opens and changes from the longitudinally extended to the open and transversally and for example, spherically expanded configuration.

Additionally or otherwise, the multielectrode system may further include conductors including or being made of a shape memory alloy configured to switch between the longitudinally extended and the transversally, spherically or conically expanded configuration.

Additionally or otherwise, the multielectrode system may further include conductors being coated by a thermally shaped polymer configured to switch between the longitudinally extended and the transversally, spherically or conically expanded configuration.

The multielectrode system may further include a sheath around the conductors also in the distal portion of the multielectrode system, which can be partially removed to expose the ring electrodes or ring electrode portions. The exposed ring electrode portions can be configured, for example, stimulation, detection and/or the like. The ring electrode portions can have various shapes and are in one embodiment round. The ring electrode portions can be at least partially arranged axially above each other, but also all other arrangements are possible.

The multielectrode system may further include a sub-sheath at least partially around at least one conductor and one ring electrode in the distal portion of the multielectrode system, which can be partially removed to expose the ring electrodes or ring electrode portions.

The multielectrode system may further include a tip electrode, which is formed by an electrical connection between either at least one of the conductors or the guidewire or a sub-guidewire with a distal tip portion of the multielectrode system. The distal tip portion of the multielectrode system can however also be only mechanically connected to the conductors and the guidewire, so that the distal tip portion does not form an additional electrode.

In an example, a diameter of the multielectrode system is in a range between 0.5 and 2.5 mm and the multielectrode system includes between 2 and 150 ring electrodes.

A diameter of a conductor may be in a range of 15 to 250 μm and in one embodiment in a range of 20 to 120 μm.

In an example, a number of conductors within the sheath forming a conductor bundle is between 1 and 100 and in one embodiment between 1 and 50.

A number of conductor bundles per multielectrode system may be in a range of 2 to 50 and in one embodiment in a range of 2 to 19.

The multielectrode system may be manufactured in various configurations, as for example 6×6, which means six ring electrodes with each having six exposed ring electrode portions and six corresponding conductors, which sum up to 36 ring electrode portions. The multielectrode system may additionally have a tip electrode.

All wires, sub-wires, guidewires and sub-guidewires may include or may be Pt, Ir, Ta, Pd, Ti, Fe, Au, Mo, Nb, W, Ni, Ti and/or the like. All wires, sub-wires, guidewires and sub-guidewires may include or may be MP35, 316L, 301, 304 and/or the like. All insulations may include or may be fluoropolymer, polyimide, polyurethane and/or the like. All sheaths and sub-sheets may include or may be PET, fluoropolymer, polyimide, polyurethane and/or the like. All ring electrodes and the tube may include or may be Pt, Ir, Ta, Pd, Ti, Fe, Au, Mo, Nb, W, Ni, Ti, MP35, 316L, 301, 304 and/or the like.

According to one embodiment, also a multielectrode unit is presented. The multielectrode unit includes a multielectrode system as described above and a pulse generator configured to control the microlead. The pulse generator can be understood as an electronic circuit or a piece of electronic equipment used to generate (rectangular) pulses.

According to one embodiment, also a use of a multielectrode system or a multielectrode unit as described above for applications within the fields of neuro modulation, electrophysiology, cardiac rhythm management, hearth stimulation, EP mapping, ablation catheter, brain stimulation, medulla stimulation, stomach stimulation and the like is presented.

It shall be understood that the manufacturing method for a microlead, the microlead, the microlead system including such microlead and the use of such microlead or microlead system according to the independent claims have similar and/or identical in one embodiment, for example, as defined in the dependent claims. It shall be understood further that in one embodiment can also be any combination of the dependent claims with the respective independent claim.

These and other aspects of one embodiment will become apparent from and be elucidated with reference to the embodiments described hereinafter.

Figure 1:
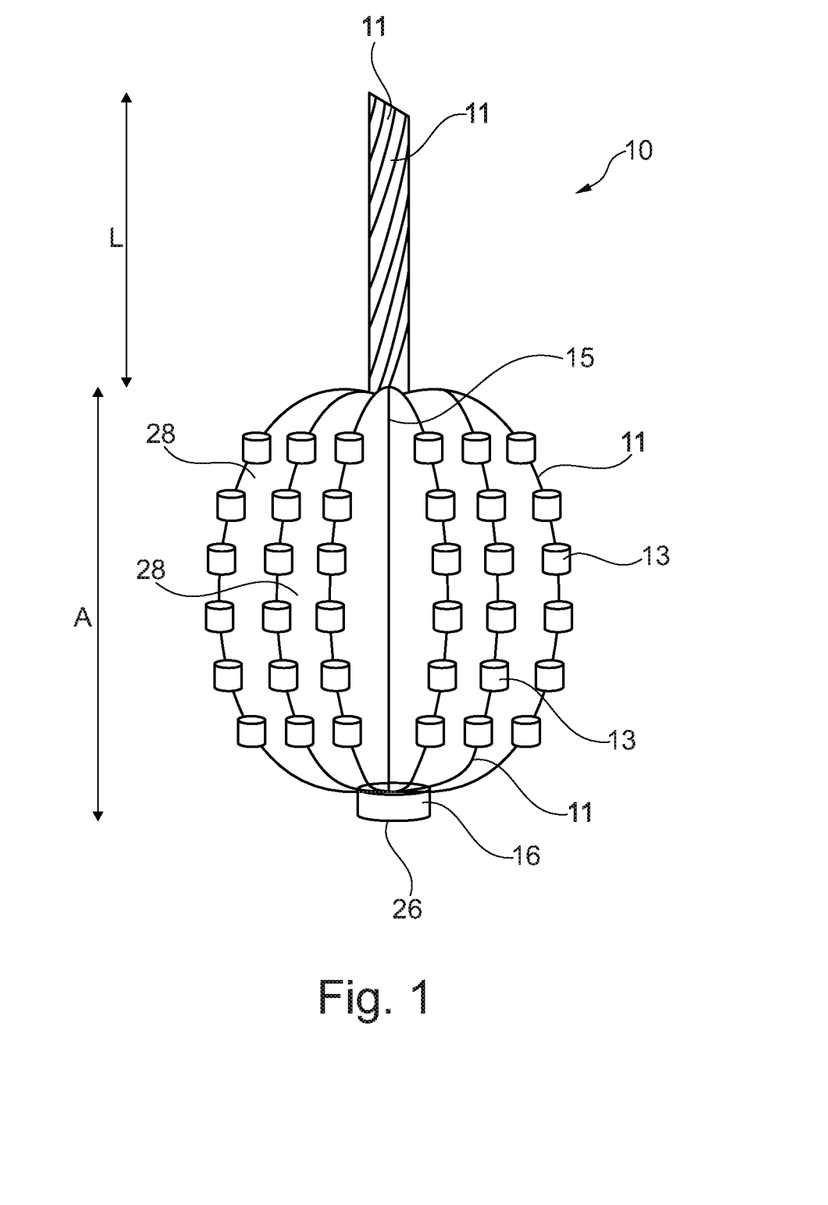
FIG. 1 illustrates schematically and exemplarily a multielectrode system according to one embodiment.
Figure 2:
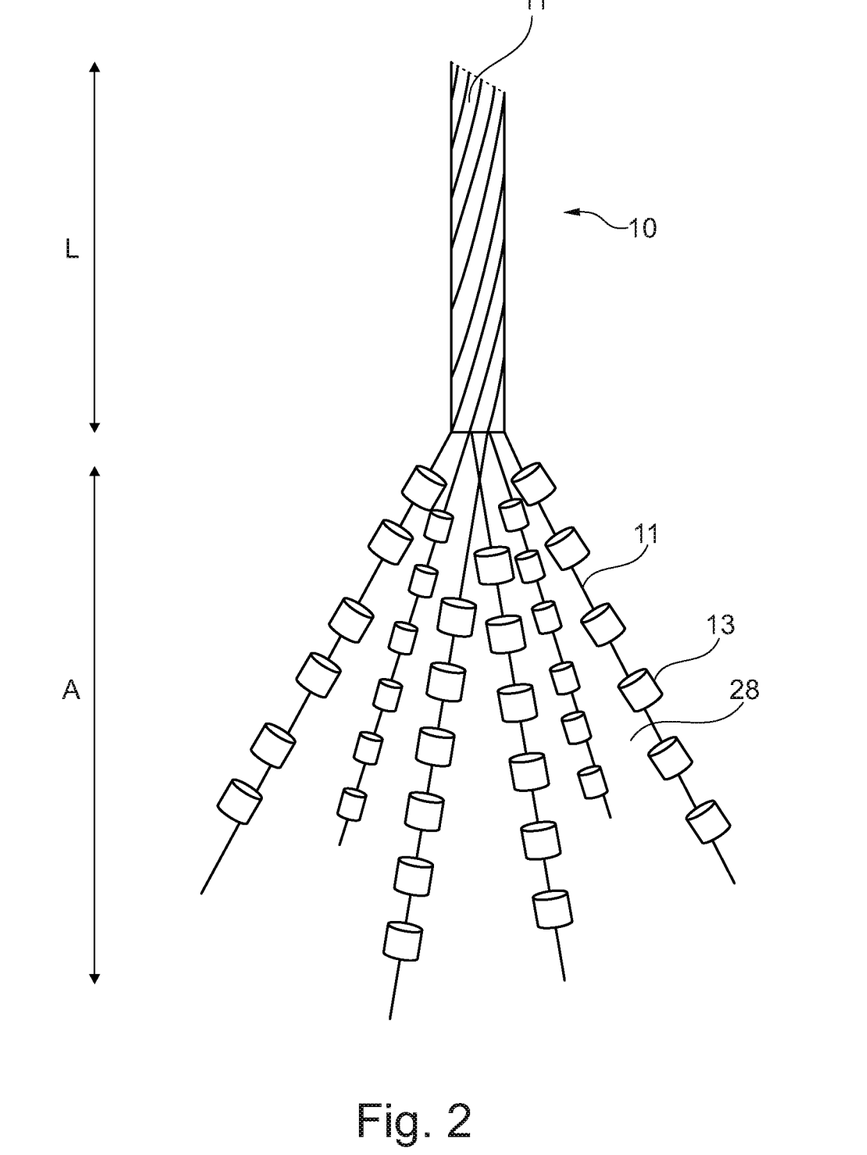
FIG. 2 illustrates schematically and exemplarily another multielectrode system according to one embodiment.
Figure 3:
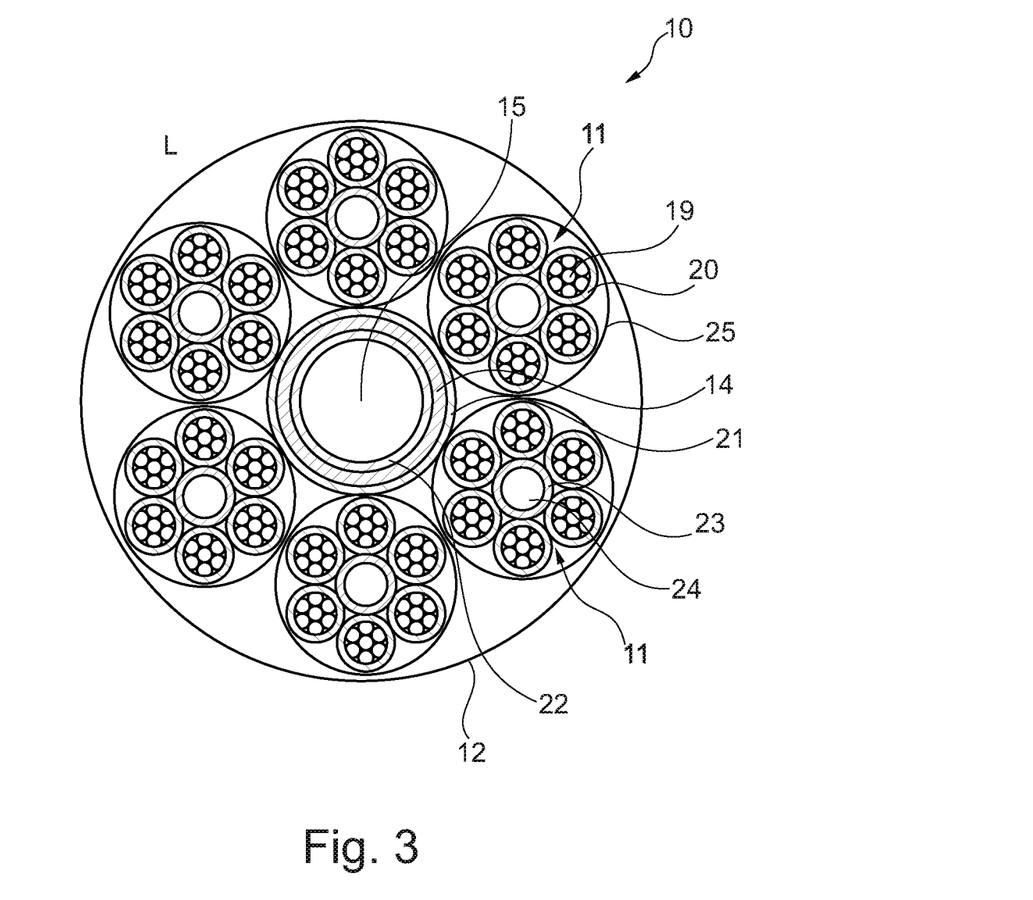
FIG. 3 illustrates schematically and exemplarily a cross-section through a proximal portion of the multielectrode systems and illustrates thereby a lead of the multielectrode system according to one embodiment.
Figure 4:
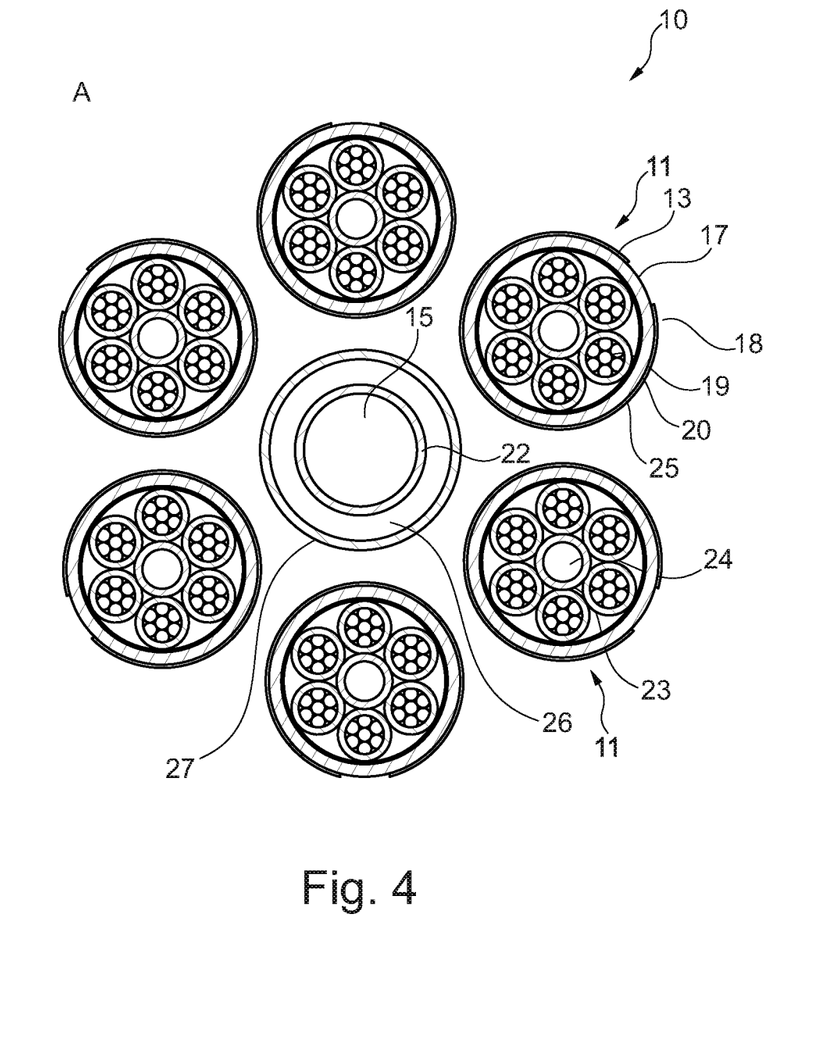
FIG. 4 illustrates schematically and exemplarily a cross-section through a distal portion of the multielectrode system and illustrates thereby a multielectrode array of the multielectrode system according to one embodiment.

The multielectrode system 10 as illustrated in FIGS. 1 and 2 includes a longitudinally extending lead L illustrated in more detail in FIG. 3 and a multielectrode array A illustrated in more detail in FIG. 4. The lead L can be understood as a cable. The multielectrode array A can be understood as an area including several independent electrodes that can stimulate, detect and/or the like. The multielectrode array A can change between a longitudinally extended configuration, for example, an insertion process into a lumen, and a spherically (FIG. 1) or conically (FIG. 2) expanded configuration, for example, an operation modus. The spherically or conically expanded configuration can be understood as a partially open configuration including accessible slits 28 between adjacent conductors 11.

FIG. 1 illustrates schematically and exemplarily a multielectrode system 10 according to one embodiment. The multielectrode system 10 includes several conductors 11, which are electrically conductive in their longitudinal direction. The conductors 11 are electrically insulated in a direction perpendicular to their longitudinal direction.

The multielectrode system 10 further includes a sheath 12 (illustrated in FIG. 3) surrounding the conductors 11 to form a conductor bundle configured as a lead L of the multielectrode system 10.

The multielectrode system 10 further includes several ring electrodes 13 each surrounding one of the conductors 11 at a distal portion of the multielectrode system 10. The ring electrodes 13 are electrically connected to the conductors 11 to form a multielectrode array A of the multielectrode system 10. The ring electrodes 13 arranged at one of the conductors 11 may be individually addressed. In other words, the ring electrodes 13 arranged along one conductor 11 may be electrically connected to the conductor 11 independently from each other.

The multielectrode system 10 can be provided with a very small diameter to avoid injuries of a venous, arterial, or lymphatic network. The diameter can be below or equal to 1.2 mm. Such small multielectrode systems 10 can still be provided with a high number of electrodes.

The multielectrode array A is configured to be in a longitudinally extended (not illustrated) or in an illustrated spherically expanded configuration. The spherically expanded configuration has a partially open shape including free slits between adjacent conductors 11. These slits 28 are accessible for tissue, nerve cells, drugs, molecules etc. and prevent that the multielectrode system 10 acts as a harmful barrier that prevents ingrowth, diffusion etc. and increases the risk of inflammatory reactions.

There are several options to have the multielectrode array A in a longitudinally extended or in a spherically expanded configuration. The multielectrode system 10 can further includes a tube 14 (illustrated in FIG. 3) extending within the conductor bundle and a guidewire 15 extending within the tube 14 and the multielectrode array A. The guidewire 15 is attached to a distal tip portion 16 of the multielectrode system 10 so that a pulling of the guidewire 15 leads to a change of the multielectrode array A from the longitudinally extended to the spherically expanded configuration. The lead L may be inserted into a body lumen by means of the guidewire 15 and a catheter. After positioning, the guidewire 15 may be retracted, so that the multielectrode array A opens and changes from the longitudinally extended to the open and spherically expanded configuration.

The multielectrode system 10 further includes a tip electrode 26, which is formed by an electrical connection between the conductors 11 and the guidewire 15 with the distal tip portion 16 of the multielectrode system 10.

FIG. 2 illustrates schematically and exemplarily another multielectrode system 10 according to one embodiment. The multielectrode system 10 includes again several conductors 11, which are electrically conductive in their longitudinal direction and electrically insulated in a direction perpendicular to their longitudinal direction.

The multielectrode system 10 further includes a sheath 12 (illustrated in FIG. 3) surrounding the conductors 11 to form a conductor bundle configured as a lead L of the multielectrode system 10. The multielectrode system 10 further includes several ring electrodes 13 each surrounding one of the conductors 11 at a distal portion of the multielectrode system 10. The ring electrodes 13 are electrically connected to the conductors 11 to form a multielectrode array A of the multielectrode system 10.

The multielectrode array A is configured to be in a longitudinally extended (not illustrated) or in an illustrated conically expanded configuration. The conically expanded configuration has a partially open shape including free slits between adjacent conductors 11. These slits 28 are accessible for tissue, nerve cells, drugs, molecules etc. and prevent that the multielectrode system 10 acts as a harmful barrier that prevents ingrowth, diffusion etc. and increases the risk of inflammatory reactions.

FIG. 3 illustrates schematically and exemplarily a cross-section through the proximal portion of the multielectrode system 10 and thereby a cross-section through the lead L of the multielectrode system 10 according to one embodiment. The lead L includes in its center the guidewire 15 and an electrical guidewire insulation 22 as well as the tube 14 and an electrical tube insulation 21.

Around this center of tube 14 and guidewire 15, six conductors 11 are arranged. All conductors 11 together are surrounded by the sheath 12, which is a heat shrink to form the conductor bundle acting as the lead L of the multielectrode system 10.

Each single conductor 11 is a bundle of six strands each including seven wires 19. The bundle of strands and thereby the conductor is surrounded by a strand sheath 25. Each strand includes an electrical strand insulation 20. The bundle of strands surrounds a sub-guidewire 24 and its electrical sub-guidewire insulation 23. The sub-guidewire 24 may further ease the pulling back of the (sub-) guidewire(s) and the change of the multielectrode array A from the longitudinally extended to the spherically expanded configuration.

FIG. 4 illustrates schematically and exemplarily a cross-section through the distal portion of the multielectrode system 10 and thereby a cross-section through the multielectrode array A of the multielectrode system 10 according to one embodiment. The multielectrode array A includes in its center the guidewire 15 and its electrical guidewire insulation 22. In the cross-section, also the tip electrode 26 and its tip electrode insulation 27 are visible. The tube 14 and the electrical tube insulation 21 do not extend to the multielectrode array A and are therefore not visible. Also, the sheath 12 surrounding all conductors 11 to form the conductor bundle is here not present in the multielectrode array A.

Around the center, the six conductors 11 each including strands of wires 19 are illustrated. Also, the electrical strand insulations 20, the sub-guidewires 24 and their electrical sub-guidewire insulations 23 as well as the strand sheaths 25 are visible.

Additionally, the multielectrode array A of the multielectrode system 10 includes six ring electrodes 13 each surrounding one of the six conductors 11. The ring electrodes 13 are electrically connected to the conductors 11 to form the multielectrode array A.

The multielectrode array A here is further provided with a sub-sheath 17 around each set of conductor 11 and ring electrode 13. The sub-sheaths 17 are partially removed around each conductor 11 to expose the ring electrodes 13 or ring electrode portions 18. The exposed ring electrode portions 18 can be configured, for example, stimulation, detection and/or the like.

Figure 5:
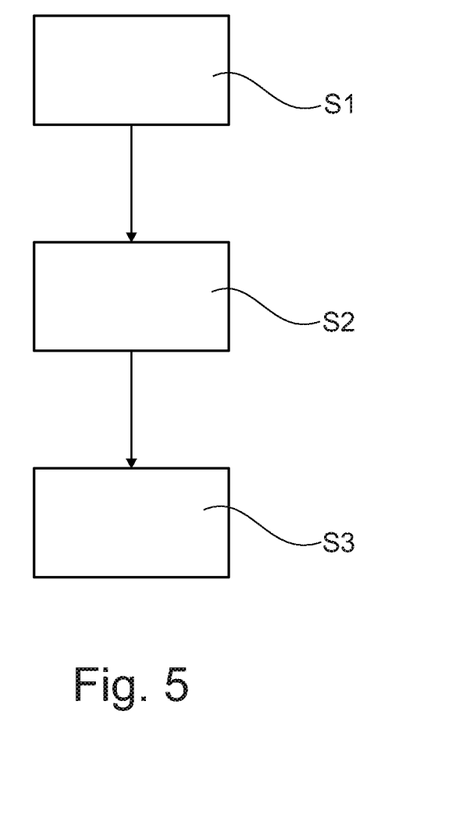
FIG. 5 illustrates a schematic overview of steps of a manufacturing method for a multielectrode system according to one embodiment.

FIG. 5 illustrates a schematic overview of steps of a manufacturing method for a multielectrode system 10 according to one embodiment. The method includes the following:

In a first step S1, providing several conductors 11, which are electrically conductive in their longitudinal direction.

In a second step S2, bundling the conductors 11 at a proximal portion of the multielectrode system 10 by means of a sheath 12 surrounding the conductors 11 at least partially to form a conductor bundle configured to be used as a lead L of the multielectrode system 10. The bundling is here a heating of a heat shrink used as the sheath 12.

In a third step S3, providing several ring electrodes 13 each surrounding one of the conductors 11 at least partially at a distal portion of the multielectrode system 10 and electrically connecting the ring electrodes 13 and the conductors 11 to form a multielectrode array A of the multielectrode system 10. The electrical connecting of the ring electrode with the conductor can be a welding, gluing, mechanically pressing, crimping or the like.

The multielectrode array A is configured to be in a longitudinally extended configuration or in a transversally and for example, spherically or conically expanded configuration. The longitudinally extended configuration can be configured for an insertion process into a lumen. The transversally and for example, spherically or conically expanded configuration can be configured for an operation modus and can be understood as a partially open configuration including accessible slits 28 between adjacent conductors 11.

The present manufacturing method for a multielectrode system 10 is less complex than conventional manufacturing methods and allows manufacturing multielectrode systems 10, which are more reliable and long-term stable than multielectrode systems 10 manufactured according to conventional manufacturing methods system. For example, an improved corrosion resistance may be achieved in comparison to a multielectrode system 10 manufactured by a conventional thin-film process.

Additionally, an improved multielectrode array A can be manufactured, because the transversally and for example, spherically or conically expanded configuration has a partially open shape including free slits 28 between adjacent conductors 11. These slits 28 are accessible for tissue, nerve cells, drugs, molecules etc. and prevent that the multielectrode system 10 acts as a harmful barrier that prevents ingrowth, diffusion etc. and increases the risk of inflammatory reactions that are dangerous and detrimental for stimulation or detection by the multielectrode array A.

It has to be noted that embodiments of one embodiment are described with reference to different subject matters. For example, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While one embodiment has been illustrated and described in detail in the drawings and foregoing description, such illustration and description are to be considered illustrative or exemplary and not restrictive. One embodiment is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

What is claimed is:

1. A manufacturing method for a multielectrode system, comprising:
    providing several conductors, which are electrically conductive in their longitudinal direction,
    bundling the conductors at a proximal portion of the multielectrode system by means of a sheath surrounding the conductors at least partially to form a conductor bundle configured to be used as a lead of the multielectrode system, and
    providing several ring electrodes each surrounding at least partially one of the conductors at a distal portion of the multielectrode system and electrically connecting the ring electrodes and the conductors to form a multielectrode array of the multielectrode system,
    wherein the multielectrode array is configured to be in a longitudinally extended or in a transversally expanded configuration; and
    further comprising electrically connecting either the conductors and/or the guidewires with a distal tip portion of the multielectrode system to form a tip electrode of the multielectrode system, wherein the tip electrode is formed as a ring-shaped electrode and is further surrounded by a tip electrode insulation.

2. The manufacturing method of claim 1, wherein the transversally expanded configuration is a spherically or a conically expanded configuration.

3. The manufacturing method of claim 1, wherein the transversally expanded configuration is a rest position of the multielectrode array, which is changeable into the longitudinally extended configuration by inserting the multielectrode array into a sleeve or a catheter.

4. The manufacturing method of claim 1, further comprising:
    providing a tube extending within the conductor bundle,
    providing a guidewire extending within the tube and the multielectrode array, and
    attaching the guidewire to a distal tip portion of the multielectrode system so that a pulling of the guidewire leads to a change of the multielectrode array from the longitudinally extended to the transversally expanded configuration.

5. The manufacturing method of claim 1, wherein the conductors comprise a shape memory alloy configured to be in the longitudinally extended and the transversally expanded configuration.

6. The manufacturing method of claim 1, wherein the conductors are coated with a thermally shaped polymer configured to be in the longitudinally extended and the transversally expanded configuration.

7. The manufacturing method of claim 1, wherein the transversally expanded configuration of the multielectrode array is a partially open configuration comprising accessible slits between adjacent conductors.

8. The manufacturing method of claim 1, wherein the bundling is a heating of the sheath, which is a heat shrink.

9. The manufacturing method of claim 1, further comprising:
providing the sheath around the conductors also in the distal portion of the multielectrode system, and
partially removing the sheath to expose at least a ring electrode portion of one of the ring electrodes.

10. The manufacturing method of claim 1, further comprising:
providing at least one conductor and one ring electrode in the distal portion of the multielectrode system at least partially with a sub-sheath, and
partially removing the sub-sheath to expose at least a ring electrode portion of the ring electrode.

11. A multielectrode system, comprising:
several conductors, which are electrically conductive in their longitudinal direction,
a sheath surrounding the conductors at least partially to form a conductor bundle configured as a lead of the multielectrode system, and
several ring electrodes each surrounding one of the conductors at a distal portion of the multielectrode system at least partially, wherein the ring electrodes are electrically connected to the conductors to form a multielectrode array (A) of the multielectrode system, and
wherein the multielectrode array is configured to be in a longitudinally extended or in a transversally expanded configuration;
wherein at least one of the several conductors is an insulated conductor, which is electrically insulated in a direction perpendicular to its longitudinal direction;
wherein at least one of the several conductors is a strand of several wires or a bundle of several strands comprising several wires; and
wherein at least one of the wires or one of the strands is electrically insulated in a direction perpendicular to its longitudinal direction; and
wherein at least one of the conductors or the guidewire is electrically connecting with a distal tip portion of the multielectrode system to form a tip electrode of the multielectrode system, wherein the tip electrode is ring-shaped and further surrounded by a tip electrode insulation.

12. The multielectrode system of claim 11, wherein the strand and/or the bundle comprises a sub-guidewire.

13. The multielectrode system of claim 11, wherein at least one of the several conductors is a wire.

14. The multielectrode system of claim 11, wherein a diameter of the multielectrode system is in a range between 0.5 and 2.5 mm and the multielectrode system comprises between 2 and 150 ring electrodes.

15. The multielectrode system of claim 11 incorporated in a multielectrode unit further comprising a pulse generator configured to control the multielectrode system.

16. The multielectrode system of claim 11 used for applications within the fields of neuro modulation, electrophysiology or cardiac rhythm management.

* * * * *